United States Patent [19]

Throckmorton et al.

[11] 4,039,565

[45] Aug. 2, 1977

[54] QUATERNIZED AMIDOAMINES

[75] Inventors: Peter E. Throckmorton; J. W. Sigan, both of Worthington, Ohio; Robert B. McConnell, Janesville, Wis.

[73] Assignee: Ashland Oil, Inc., Ashland, Ky.

[21] Appl. No.: 590,514

[22] Filed: June 26, 1975

[51] Int. Cl.[2] .................... C07C 141/06; C07C 91/26; C07C 103/38

[52] U.S. Cl. .......................... 260/459 A; 260/501.15; 260/534 M; 260/558 R; 260/558 P; 260/561 R; 260/562 R; 260/562 A; 427/430 R

[58] Field of Search .......... 260/558 R, 561 R, 459 A, 260/501.15, 558 P, 562 R

[56] References Cited

U.S. PATENT DOCUMENTS

| | | | |
|---|---|---|---|
| 2,233,296 | 2/1941 | Nelles et al. | 260/561 R X |
| 2,648,708 | 8/1953 | Steiger | 260/558 R |
| 2,947,748 | 8/1960 | Zeitschel | 260/459 A X |
| 3,005,850 | 10/1961 | Wright, Jr. | 260/562 S |
| 3,016,382 | 1/1962 | Wright, Jr. et al. | 260/562 R X |
| 3,083,143 | 3/1963 | Schmid et al. | 260/561 R X |
| 3,632,623 | 1/1972 | Becke et al. | 260/459 A |
| 3,661,966 | 5/1972 | Bartmann et al. | 260/561 R X |
| 3,714,249 | 1/1973 | Norton | 260/558 R |
| 3,936,503 | 2/1976 | Miller, Jr. et al. | 260/501.15 X |

OTHER PUBLICATIONS

Steiger, CA 46:140f (1952) - see U.S. Pat. No. 2,551,647.

*Primary Examiner*—Daniel E. Wyman
*Assistant Examiner*—Thomas A. Waltz

[57] ABSTRACT

Quaternary compounds having the structure

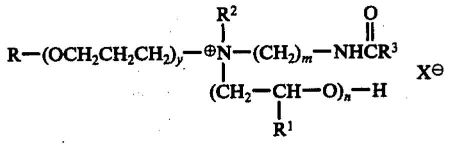

are useful as fabric softeners.

4 Claims, No Drawings

QUATERNIZED AMIDOAMINES

BACKGROUND OF THE INVENTION

1. Field of the Invention

This invention relates to quarternary compounds prepared by the quaternization of amidoamines and to their use as fabric softeners and anti-stats.

2. Description of Prior Art

Quaternary nitrogen compounds have found commercial acceptance for fabric softening. The washing of fabrics, especially when machine washing is used, tends to cause surface roughness in the fabric making the fabric harsher to the touch. Addition of fabric softeners tends to overcome this undesirable effect resulting in a softer, fluffier fabric after washing and drying. Softeners can be of three types, cationics, nonionics and anionics. Nonionics in general are not as efficient softeners but do have the advantage of higher resistance to yellowing. Anionics, such as stearic acid soaps have also been used. However, the cationic softeners, especially the quaternary nitrogen compounds, have found the highest commerical acceptance. These cationics have the most acceptable combination of properties, including dispersability in water, substantive deposition on the fabric from a water carrier, resistance to yellowing, ability to be removed with subsequent washings, stability as a concentrate for industrial handling and shipment, and stability as a dispersion of 3–6% concentration. The types of cationics which have been found useful include primary amine salts, salts of tertiary amines, quaternary ammonium salts, and quaternary salts of amidoamines. In this last category, a compound of the structure:

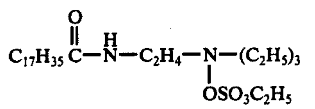

has been of commercial importance (Textile Chemicals and Auxiliaries Speel and Schwartz, Reinhold Publishing Corp., New York, 1957, pp 396–401).

SUMMARY OF THE INVENTION

In accordance with this invention, compounds of structure I

I

-continued

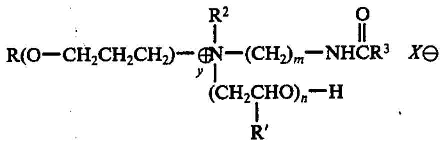

wherein: R is alkyl, aralkyl, alkyaryl or alkoxyalkyl; R′ is alkyl, alkoxy- alkyl,, hydroxyalkyl or hydrogen; $R^2$ is alkyl, benzyl, carboxymethyl; $R^3$ is alkyl, aralkyl, alkyaryl, or carboxyalkyl; X is a negatively charged ion; *m* is 2 or 3; *y* is 0 or 1; *n* is 1–15 have been found to be excellent fabric softeners. These quaternaries are most easily prepared from the corresponding amidoamines of structure II.

II

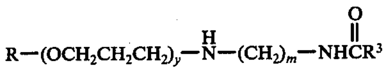

Compounds of Structure II are prepared most easily from the reaction of the corresponding acid, ester, or anhydride with the corresponding diamine according to the reaction sequence:

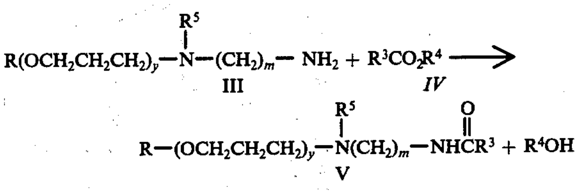

$R^3$ of the acid reactant can be alkyl, aralkyl, alkyaryl, aromatic or alkoxyalkyl, while $R^4$ can be hydrogen, alkyl or acyl and $R^5$ equals hydrogen or $R^2$. The amine nitrogens of reactant III can be separated from each other either by two or three methylenes (*m* can be either 2 or 3). The quaternization of the amidoamines is easily carried out with standard alkylating agents such as methyl chloride or dimethyl sulfate together with an alkoxylation step.

DESCRIPTION OF THE PREFERRED EMBODIMENTS

The reaction sequences suitable for the preparationn of the composition of this invention are shown in Reaction Scheme I. Although not exhaustive of the possible routes, it represents the easiest or most economic routes to the subject composition. For convenience in understanding the processes involved, Reaction Scheme I divides the various stages of the reactions into Reactions A, B, C and D.

Reaction Scheme I
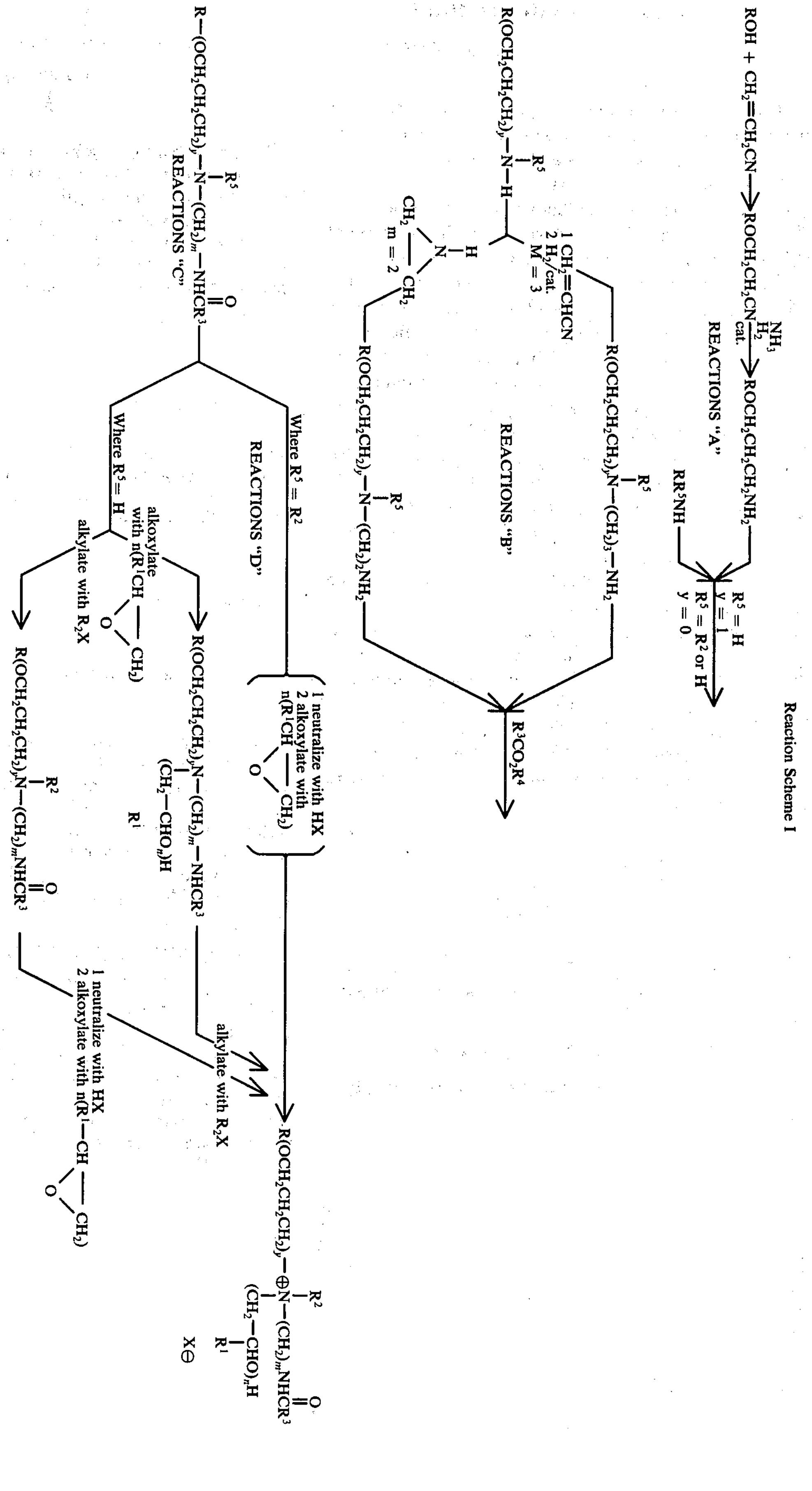

Reactions A involves the preparation of the starting amine. In those cases where in Compound I *y* is 1, the starting amine is formed by the cyanoethylation and subsequent hydrogenation of an alcohol. This cyanoethylation of alcohols is well known in the art, and is clearly explained in "The Chemistry of Acrylonitrile" 2nd ed., American Cyanamid Co., 1959, p. 24. Cyanoethylation of amines is described in "Cyanoethylation", Organic Reactions, John Wiley and Sons, New York (1949). In the hydrogenation of the nitriles to amines, the presence of ammonia is advisable to suppress the formation of higher amines (*J. Am. Chem. Soc.* 82, 2386 (1960)).

In those cases where no ether oxygen is desired in the final product (i.e., where $y = o$), primary ($R^5 = H$) or secondary ($R^5 32\ R^2$) amines can be used. The R group on these starting amines can be alkyl, aralkyl, alkyaryl or alkoxy- alkyls. It is evident that $R^5$ and R can be part of the same cyclic structure (e.g. piperidine, tetrahydropyrrole, tetrahydroquinoline, oxazoline) without departing from the spirit of the invention. It is also evident that polyalkylene oxides can also serve as the starting material for the cyanoethylation to the primary amine.

Reactions B provide for the conversion of the amine starting material to the corresponding diamine III. In those cases where a substituted propylene diamine is desired, an amine or etheramine is cyanoethylated and subsequently hydrogenated by procedures previously described. In those cases where a substituted ethylene diamine is desired, the amine or etheramine is hydrogenated by procedures previously described. In those cases where a substituted reacted with ethylene imine. The reaction of primary amines with ethyleneimine is described in an article by G. Braz and V. Skovadumov, *Dokl. Akad. Nauk. S.S.S.R.* 59, 489 (1948); *cf, Chem. Abstr.* 42, 6747. Reaction of secondary amines is described in an article by A. McKay et. al., *Can. J. Chem.*, 34, 1567 (1956).

Reactions C represent the conversion of the secondary-primary diamine or the tertiary-primary diamine to an amidoamine. This conversion of diamines to amidoamines is well known in the art, and is described in U.S. Pat. No. 3,855,235 as an intermediate step in the preparation of diimidazolines from triamines.

The preparation of the amidoamine is not a simple reaction. In cases where the starting amine is a secondary-primary diamine, some tertiary amide tends to form.

$$RNH-(CH_2)_m-NH_2 + R^3CO_2R^4 \longrightarrow RNH\ (CH_2)_m-NH\overset{\overset{O}{\|}}{C}R^4 + R-\underset{\underset{O=CR^3}{|}}{N}-(CH_2)_m-NH_2$$

The alternative of using a tertiary-primary diamine precludes the formation of this by-product. This advantageous reduction of the level of tertiary amide by-product must be balanced against the frequently higher cost of the starting secondary amine in comparison with the normally lower cost of the primary amine.

Alternatively, some of the aminoamide may cyclize under the conditions of amide formation to yield the corresponding tetrahydropyrimidine.

Reactions D represent the conversion of amidoamine to the quaternary composition of this invention. In those cases where the diamine comprises a tertiary amine (where $R^5$ is the same as $R^2$) together with a primary amide, alkoxylation with n moles of alkylene oxide leads directly to the compositions of this invention (I).

In those cases where the diamine comprises a secondary amine ($R^5$ is equal to hydrogen) together with a primary amido group, both an alkylation and an alkoxylation must be carried out. As shown in Reactions D, either one may be done first. Alkoxylation procedures are well known in the art, and can use either single alkylene oxides or mixtures. The alkoxylation of secondary amines is well described in U.S. Pat. No. 3,456,013. Alkylation of tertiary amines to the quaternary compounds is a standard commercial procedure, and the conversion of alkoxylated secondary amine to the quaternary derivative is described in U.S. Pat. No. 3,428,682.

The following Preparations and Examples are illustrative of the preparation of the compositions of this invention.

Preparation of Compound (a)

N-(tridecycloxypropyl)-1,3-propylene diamine

Cyanoethylation: To 1000 g (5 moles) of tridecanol (branched OXO alcohol derived from trimerized isobutylene) was added 5.3 g of sodium methoxide as a 25% solution in alcohol. Then over a period of 3 hours there was added, with stirring, 292 g (5.52 mol) of acrylonitrile at 45°. The mixture was allowed to react an additional 3 hours. The reaction mixture was then vacuum stripped at 93° C to remove volatiles and filtered. The residue remaining was found to contain 0.25% OH (calculated, 0%). Hydrogenation: 1000 g of said residue and 10 g of a commercial grade of wet Raney nickel mud was charged to a stainless steel autoclave, sealed, evacuated and pressured to 300 psig ammonia at 138° C. With continuous stirring the autoclave was held at 500–600 psig $H_2$ for 4.5 hours at 138°–149°; by this time 92% of theoretical hydrogen uptake, as measured by titrating a sample for amine, was completed. The autoclave was quenched, cooled and the product was filtered. The filtrate was a fluid, liquid amine; percent nitrogen as found by titration 5.26% N; calculated, 5.44% N.

Cyanoethylation: The liquid amine product in the amount of 800 g (3.02 mol) was charged again to the autoclave with 168 g (3.17 mol) of acrylonitrile, 8 g wet Raney nickel mud together with 40 g water. The autoclave was sealed and held at 55°–70° C for 2 hours. The resulting nitrile was hydrogenated as previously described, yielding the N-alkoxy-propylene diamine containing 4.21% primary amine, 4.15% secondary amine and 0.087% tertiary (calculated values 4.45%, 4.45% and 0%).

Preparation of Compound (b)

N-cetyl- 1,3-propylene diamine

Cetyl amine was cyanoethylated and hydrogenated by the procedures previously described, yielding the N-alkyl propylene diamine; 4.36% primary amine, 4.75% secondary and 0.75% tertiary; calculated 4.7%, 4.7%, and 0%.

Preparation of Compound (c)

Mixture of N-(tridecyloxy propyl)-N'-(stearoyl)-propylene diamine and the corresponding tetrahydropyrimidine N-tridecycloxypropyl-13-propylene diamine (85 g, 0.27 mole, Compound a) and stearic acid (143 g, 0.5 mole) were charged to a glass vessel, and a nitrogen sparge was started. The reaction mass was heated to 150° C, held for 2 hours at which time the primary amine value was 0%, secondary amine was 0.64%, and tertiary was 0.73%; calculated for the diamine; 0%, 1.67% and 0%. Heating was continued for an additional 4 hours at 150° C under the nitrogen sparge, resulting in cyclization of a substantial portion of the aminoanide to the corresponding tetrahydropyrimidine. This mixture showed a nitrogen analysis of 0.11% primary, 0.13% secondary and 1.15% tertiary. For complete cyclization to the tetrahydropyrimidine, the calculated analysis is 0% primary, 0% secondary and 1.72% tertiary. The increase in the tertiary amine content is good evidence of cyclization of a substantial portion of the aminoamide.

Preparation of Compound (d)

N-cetyl-N'-stearoyl-propylene diamine

The procedure used for the preparation of Compound (c) was followed using 75 g (0.2 mole) of compound (b) and 70 g (0.2 mole) of methyl stearate (95% $C_{18}$). The reaction was continued for 11 hours at 125°-155° C, yielding a viscous amide product. Primary amine nitrogen was 0.52%, secondary was 1.35%, and tertiary 0.92%. Calculated for this amide; primary, 0%; secondary 2.48%, tertiary, 0%.

Preparation of Compound (e)

N-cetyl-N'-acyl propylene diamine from tallow

This procedure was the same as used for Compound (d) with the exception that tallow was used as the ester and compound (b) as the diamine. The analysis showed 0.4% primary nitrogen, 1.51% secondary nitrogen and 0% tertiary. Calculated is 0%, 2.4%, and 0%.

EXAMPLE 1

Alkoxylation and Alkylation of Compound (c)

Alkoxylation:

To a clean and dry stainless steel autoclave was charged 147 g (0.145 mol) of Compound (c), together with 200 ml isopropanol (IPA). The autoclave was then sealed, flushed with nitrogen and 20 g (0.454 moles) of ethylene oxide (EO) was charged by means of nitrogen pressure. The autoclave was then heated and stirred at 110° C under autogeneous pressure of 82 psig. After 0.75 hour the pressure had diminished to 60 psig. No further pressure diminishment was observed on additional heating for 1.25 hours. The autoclave was then cooled and the product was vacuum distilled to remove IPA and unreacted EO. There was obtained 166.6 g of alkoxylated product. Amine nitrogen by titration was 1.01% N.

Alkylation:

To 165 g (0.199 mol) of the alkoxylated product was slowly added with stirring 13.5 g (0.107 mol) of dimethyl sulfate at a rate which maintained the temperature 25°-35° C during 0.75 hour and stirred for an additional 1 hour at 30° C. There was obtained about 178 g of a viscous product which was treated with 8.2 g of 50% hydrogen peroxide and heated under vacuum at 80°-85° C to decompose any residual peroxide. Amine nitrogen by titration was 0.19% N. IPA was added to form a 90% active solution for water dispersiblity, washing and softening tests. The product was found to be readily dispersible in water to provide stable 6% dispersions at temperatures over the range 70°-120°.

EXAMPLE 2

Alkoxylation and Alkylation of a Mixture of Compounds (d) and (e)

Following the same procedure as for Example 1, a mixture of compounds (d) and (e) was ethoxylated and quaternized.

Product Evaulation

The dispersion stability of the compounds of this invention was evaluated by adding melted softener to water (120° F, 150 ppm hardness) with agitation. The dispersion were held at 70° F, 105° F and 120° F for 4 weeks. The stabilities are shown in Table II.

Representative softeners were evaluated for softening ability with the results shown in Table III. The control A used was VARISOFT 222 (Trademark of Ashland Oil, Inc), Control B was dimethyl dihydrogenated tallow ammonium chloride. The fabric to be treated (sheets and towels) were washed in a standard washing machine, and sufficient softener was added to the water at the beginning of the rinse cycle to provide .1% active softener based on the cloth weight. The rinsed towels were dried in an automatic dryer and stored for 24 hours prior to evaluation by a test panel. A rating of 1 represents the harshest feel, while 5 represents the softest.

Table I

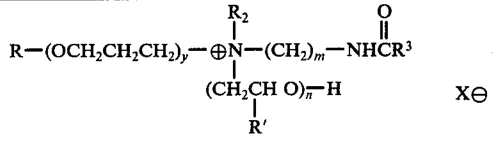

R'=H; $R^2=CH_3$; m=3, X−= $CH_3SO_4^{\ominus}$

| Example | R | y | n | $R^3C(=O)$ |
|---|---|---|---|---|
| 1 | tridecyl | 1 | 3 | stearyl |
| 2 | cetyl | 0 | 2.9 | mixed stearyl-tallow |
| 3 | tallow | 0 | 3 | tallow |
| 4 | lauryl | 1 | 3.8 | stearyl |

Table II

| Composition of Example | Time | Dispersion Stability of Experimental Softener 3% 120° | 3% 105° | 3% 70° | 6% 120° | 6% 105° | 6% 70° |
|---|---|---|---|---|---|---|---|
| 1 | 1 day | 5% Split | 5% Split | 5% Split | Stable | Stable | Stable |
| | 10 day | 5% Split | 7% Split | 13.5% Split | Stable | Stable | Stable |
| | 3 Wk. | — | — | — | Stable | Stable | Stable |
| 2 | 1 Wk. | 20% Split | — | — | Stable | — | — |
| | 2 Wk. | 20% Split | — | — | Stable | — | — |
| | 4 Wk. | 20% Split | — | — | Stable | — | — |

Table II-continued

Dispersion Stability of Experimental Softener

| Composition of Example | Time | 3% 120° | 3% 105° | 3% 70° | 6% 120° | 6% 105° | 6% 70° |
|---|---|---|---|---|---|---|---|
| 3 | 1 day | 18% Split | 18% Split | 18% Split | | | |
| | 1 Wk. | — | — | — | Stable | Stable | Stable |
| | 2 Wk. | — | — | — | Stable | Stable | Stable |
| | 3 Wk. | — | — | — | Stable | Stable | Stable |
| 4 | 1 Wk. | Stable | Stable | Stable | Stable | Stable | Stable |
| | 2 Wk. | Stable | Stable | Stable | Stable | Stable | Stable |
| | 3 Wk. | Stable | Stable | Stable | Stable | Stable | Stable |

Table III

Fabric Softening Results

| Composition of Example | Rating* |
|---|---|
| 1 | 2.0 |
| 2 | 3.8 |
| 3 | 3.0 |
| 4 | 2.0 |
| Control A | 3 |
| Control B | 5 |

A VARISOFT 222, Trademark of Ashland Oil, Inc.
B Dimethyl dihydrogenated tallow ammonium chloride.
*5 = softest; 1 = harshest

What is claimed is:

1. A compound having the formula:

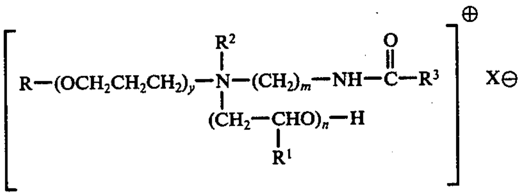

wherein:
R and $R^3$ are each $C_1$–$C_{22}$ alkyl
$R^1$ is methyl or hydrogen
$R^2$ is methyl or benzyl
X is a negatively charged ion *m* is 2 or 3
*y* is 0 or 1
*n* is 1–15

2. A compound in accordance with claim 1 wherein *y* is 0; $R^1$ is hydrogen; $R^2$ is methyl and X is methyl sulfate.

3. A compound in accordance with claim 1 wherein *m* is 3 and *n* is 1–5.

4. A compound in accordance with claim 3 wherein *y* is 1.

* * * * *